United States Patent [19]

Harding

[11] Patent Number: 5,008,911
[45] Date of Patent: Apr. 16, 1991

[54] X-RAY QUANTA MEASURING DEVICE INCLUDING DIAPHRAGM FOR PRODUCING CONICAL RADIATION BEAM ON OBJECT BEING MEASURED

[75] Inventor: Geoffrey Harding, Hamburg, Fed. Rep. of Germany

[73] Assignee: U.S. Philips Corporation, New York, N.Y.

[21] Appl. No.: 411,357

[22] Filed: Sep. 22, 1989

[30] Foreign Application Priority Data

Sep. 22, 1988 [DE] Fed. Rep. of Germany ....... 3842146
Mar. 21, 1989 [DE] Fed. Rep. of Germany ....... 3909147

[51] Int. Cl.$^5$ .......................................... G01N 23/201
[52] U.S. Cl. .......................................... 378/86; 378/88; 378/147; 378/149
[58] Field of Search .................. 378/147, 149, 86, 88, 378/89

[56] References Cited

U.S. PATENT DOCUMENTS

| | | | |
|---|---|---|---|
| 3,903,415 | 9/1975 | Holzapfel | 378/147 |
| 4,466,113 | 8/1984 | Strecker | 378/146 |
| 4,751,722 | 6/1988 | Harding et al. | 378/88 |
| 4,754,469 | 6/1988 | Harding | 378/86 |
| 4,825,454 | 4/1989 | Annis et al. | 378/147 |

FOREIGN PATENT DOCUMENTS 2003753 3/1972 Fed. Rep. of Germany.
3526015 1/1987 Fed. Rep. of Germany.
3712928 11/1988 Fed. Rep. of Germany.

*Primary Examiner*—Edward P. Westin
*Assistant Examiner*—Kim-Kwok Chu
*Attorney, Agent, or Firm*—William Squire

[57] ABSTRACT

A device for measuring the pulse transfer of X-ray quanta which are elastically scattered in an examination zone, includes an X-ray source which is arranged on one side of the examination zone, a detector which is situated on the other side of the examination zone and which measures the energy of the X-ray quanta, and a rotationally-symmetrical diaphragm device which is arranged between the detector and the X-ray source. In a device of this kind a comparatively accurate determination of the pulse transfer is also possible for thick objects, because the diaphragm device is constructed so that the X-ray quanta emitted by the X-ray beam source are transmitted to the examination zone only on the envelope of a cone.

17 Claims, 2 Drawing Sheets

– 5,008,911 –

X-RAY QUANTA MEASURING DEVICE INCLUDING DIAPHRAGM FOR PRODUCING CONICAL RADIATION BEAM ON OBJECT BEING MEASURED

BACKGROUND OF THE INVENTION

The invention relates to a device for measuring the pulse transfer spectrum of X-ray quanta which are elastically scattered in an examination zone, comprising a polychromatic X-ray source which is arranged on one side of the examination zone and a detector device which is situated on an other side of the examination zone and which measures the energy of the X-ray quanta, and also comprising two diaphragm devices which have a common symmetry axis and transmit scattered radiation to the detector only within a given scattering angle range, the first diaphragm device being arranged between the examination zone and the X-ray source whilst the second diaphragm device is arranged between the examination zone and the detector device. A device of this kind is essentially known from German patent application P 37 12 928.

It is known that scattered radiation which encloses only a small angle with respect to the primary radiation (for example, an angle of less than 10°) consists mainly of elastically scattered radiation if the energy of the X-ray quanta is not very high. Contrary to non-elastically scattered radiation (Compton scattered radiation), the energy spectrum of elastically scattered radiation corresponds to that of the primary radiation beam. The intensity of elastically scattered radiation exhibits a strong dependency on the pulse transfer which is determined by the molecular structure of the irradiated substance.

This dependency, also being different for fat and muscle tissue, is utilized by the known device in order to form a fat image and a muscle tissue image, respectively. The scattered radiation produced by a monochromatic radiation source is then measured for the pulse transfer range for which the spectrum of the relevant tissue (fat or muscle) is as large as possible whilst that for the other type of tissue (muscle or fat) is as small as possible.

The cited Application P 37 12 928 also mentions that instead of a monochromatic source there may also be provided a polychromatic gamma source or X-ray source if use is made of energyresolution detectors. The pulse transfer spectrum can thus be determined.

From such a spectrum information concerning the molecular structure of the irradiated substance, can be derived in order to identify this substance. This is useful for medical applications, for example for determining the mineral contents of bones in diagnosing osteoporosis, but also for other purposes, for example the inspection of luggage.

The pulse transfer of an X-ray quantum is at least approximately proportional to the product of the energy of the X-ray quantum and the scattering angle at which the X-ray quantum has been deflected from its previous path during the scattering process. The accuracy of determination of the pulse transfer depends inter alia on the accuracy of determination of the energy of the X-ray quantum and its scattering angle. The energy of X-ray quanta can be quite accurately measured by means of a suitable detector, for example made of germanium. In the described device the accuracy of determination of the scattering angle depends on the two diaphragm devices. The first diaphragm device is constructed so that a beam of small cross-section (pencil beam) is formed. The second diaphragm device consists of a number of laminations which are arranged on the envelopes of cones whose apices are situated on the primary beam formed in the examination zone. If the scattering angle is to be defined as accurately as possible in this manner, the lamination dimensions must be as large as possible in comparison with the thickness of the examination zone. In the case of thick objects, this implies the use of very long laminations and hence detectors having a very large diameter. Such detectors are expensive.

SUMMARY OF THE INVENTION

It is the object of the invention to construct a device of the kind set forth so that even in the case of thick objects a comparatively accurate determination of the pulse transfer is possible by means of a comparatively small detector device.

This object is achieved in accordance with the invention in that the first diaphragm device is constructed so that the X-rays on the envelope of a primary radiation cone are transmitted, the second diaphragm device being constructed so that scattered radiation produced in the examination zone is incident on the detector device in a rotationally symmetrical fashion with respect to the symmetry axis.

Thus, in accordance with the invention instead of a pencil-shaped primary beam there is formed a primary radiation beam which is situated on the envelope of a truncated cone. This allows for the second diaphragm device to be constructed so that the scattered radiation beam detected by the detector device converges towards the symmetry axis or extends parallel thereto (instead of being divergent as in the known device) so that comparatively small detectors can be used even in the case of a large distance between the detector device and the examination zone.

It is to be noted that DE-PS 20 03 753 already discloses a device for measuring scattering curves of (thin) test objects where the X-rays are influenced by a diaphragm device so that a primary radiation cone is obtained. The scattered radiation is detected, via an annular diaphragm, by a detector without energy resolution (counting tube) which is arranged on the symmetry axis of the primary beam, which diaphragm is displaceable, together with the detector, in the direction of the symmetry axis. The scattering curve of the test object can be derived from the measurement values thus obtained when use is made of monochromatic radiation. Thus, in the known device measurement takes place with constant energy and a varying scattering angle, and in accordance with the invention measurement takes place, using a fixed scattering angle or stationary diaphragm devices, in dependence of the energy of the X-ray quanta, which measurement can be performed comparatively accurately by means of a suitable detector.

In a preferred embodiment in accordance with the invention the second diaphragm device consists of a plurality of mutually enclosing cylindrical or conical collimator members which are concentric with a symmetry axis of a primary radiation cone. When the detector device comprises a plurality of concentrically arranged, preferably annular detectors which detect each time the scattered radiation passing between two collimator bodies, the scattered radiation at different depths within the examination zone can be simultaneously and efficiently measured.

BRIEF DESCRIPTION OF THE DRAWING

The invention will be described in detail hereinafter with reference to the drawings. Therein.

DETAILED DESCRIPTION OF THE PREFERRED EMBODIMENT

Figure 1:
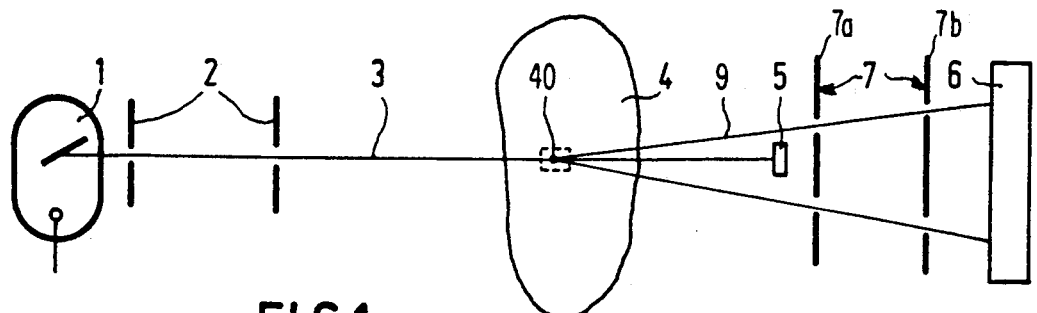
FIG. 1 shows a first embodiment in accordance with the invention.

The reference numeral 1 in FIG. 1 denotes an X-ray source whose anode (not shown) is preferably made of tungsten and carries a voltage of, for example 100 kV with respect to the cathode during operation. The major part of the X-ray quanta emitted by such an X-ray source has an energy of between 40 and 80 KeV. Between the X-ray source 1 and the object 4 to be irradiated, there is arranged a first diaphragm device which consists of a pair of axially spaced apart diaphragm plates 2 having only a point-shaped central aperture for the passage of a central primary beam of small cross-section along the symmetry axis 3. This central primary beam irradiates object 4 producing elastically scattered radiation from points proximate axis 3 including those within a small sub-volume 40 centered on symmetry axis 3. After the object 4, axially spaced apart detectors 5 and 6 are provided for respectively detecting radiation emanating from object 4 directed along the symmetry axis 3 and radiation which has been elastically scattered from sub-volume 40 along a small range of angles with respect to the symmetry axis defined by an annular secondary radiation cone 9. Cone 9 is defined by a second diaphragm device 7 between detectors 5 and 6 comprising a pair of axially spaced apart diaphragm plates 7a and 7b, having annular apertures. The annular aperture in the diaphragm plate 7a closest to the object 4 is smaller than the annular aperture in the diaphragm plate 7b more remote from object 4.

Using the device shown in FIG. 1, each time only a given sub-volume of the object can be examined. If the entire object is to be examined, either the object or the measurement device must be displaced in three mutually perpendicular directions, a measurement being performed each time.

Figure 2:
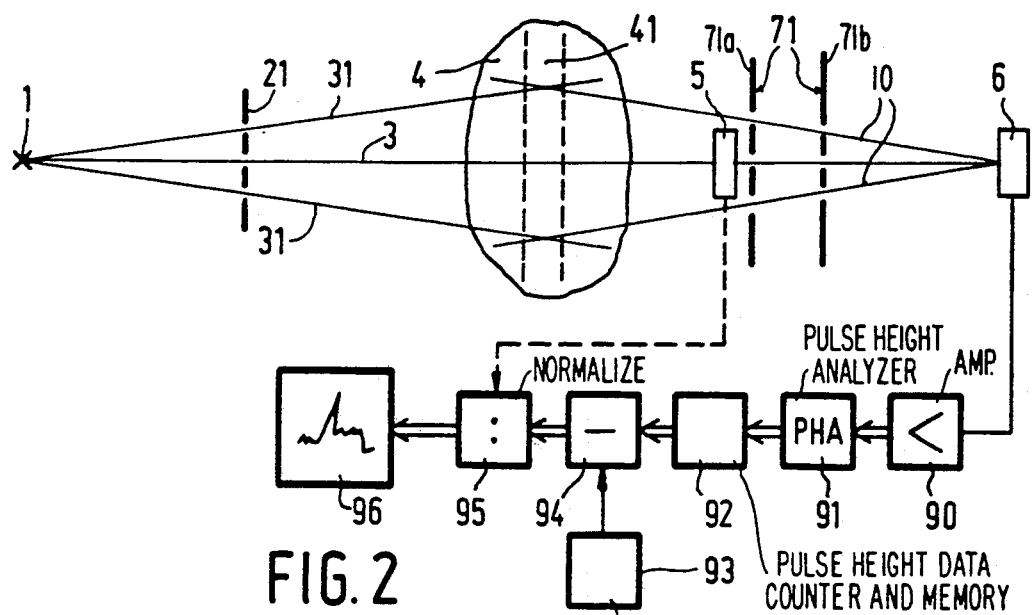
FIG. 2 shows a second embodiment, in accordance with the present invention

FIG. 2, however, shows a device which also offers spatial resolution in the object depth, i.e. in the direction of the primary beam, and which necessitates only a two-dimensional scan for the examination of a three-dimensional object. Therefore, this device is particularly suitable for inspecting luggage and the like.

In FIG. 2 a first diaphragm device comprising a single diaphragm plate 21 is provided between the source 1 and the examination zone of an object 4. Diaphragm plate 21 comprises both a circular ring-like aperture and a central point-shaped aperture for the passage of the X-rays emitted by the X-ray source 1. The X-rays passing through the ring-like aperture of the diaphragm plate 21 thus define the envelope of a primary annular radiation cone whose apex coincides with the focus of the X-ray source 1 and whose symmetry axis 3 extends through the center of the annular aperture. The point-shaped aperture of diaphragm plate 21 is for the passage of a central primary beam of small cross-section which coincides with the symmetry axis 3 of the primary annular radiation cone 31.

In the examination zone of object 4 the primary radiation generates inter alia elastically scattered radiation. A second diaphragm device 71 which comprises axially-spaced diaphragm plates 71a and 71b, is arranged between the examination zone of object 4 and a detector device 6 for separating the scattered radiation which is scattered at a defined small angle of, for example 3.6 degrees within the area of object 4 irradiated by the primary radiation cone 31. To this end, each of diaphragm plates 71a and 71b is provided with an ring-like aperture which is concentric with the symmetry axis 3. The diameter of the ring-like aperture in the diaphragm plate 71a facing the examination zone of object 4 is larger than that in the remote diaphragm plate 71b so that the second diaphragm device 71 allows for the passage of scattered radiation on the envelope of a secondary annular radiation cone 10 which opens towards the examination zone. The area of intersection of the two cones 31 and 10, having the same symmetry axis, defines a layer 41 in object 4 which is perpendicular to the primary beam 3 and wherefrom scattered radiation can reach the detector 6 through the second diaphragm device 71. The layer area in which this scattered radiation is produced is shaped as a ring which is concentric with the primary central beam 3. The diameter of this ring depends on the angle of aperture of the primary radiation cone 31 or the secondary radiation cone 10, which may each time amount to 1.8°. The dimensions of the detector 6 are then independent of the thickness or the depth of the object 4 to be examined by means of the detector 6.

The pulse transfer of the detected X-ray quantum can each time be determined by the block diagram circuit from the output signal of the energy-resolution detector, for example, a germanium detector. The output signal of the detector 6 is applied to a pulse height analyser 91 via an amplifier 90 having a suitable gain. The pulse height analyser 91 assigns a digital data word to each output pulse produced by the detector 6, which data word characterizes the amplitude of this pulse and hence the energy of the X-ray quantum. In order to characterize the energy range to be detected by the detector 6, there may be, for example 128 different data words. A unit 92 counts how often the individual data words occur during a predetermined measurement period and stores these numbers. At the end of the measurement period it thus contains 128 numbers which characterize the variation of the scattered radiation intensity as a function of the quantum energy or the pulse transfer. This series of numbers thus represents the energy spectrum or the spectrum of the pulse transfer of the elastically scattered radiation. This spectrum, however, must still be corrected in order to eliminate disturbing effects.

One of these disturbing effects consists in that the X-rays interact with the edges of the diaphragms devices 21 and 71, so that the detector 6 detects (background) radiation even when the object 4 is not present in the examination zone. This background radiation is independent of the object 4. Therefore, it can be measured once in order to be stored in a memory 93; in a circuit 94 it can then be subtracted from the result supplied by the unit 92.

A further disturbing effect consists in that in the intensity in the spectrum transmitted by the body 4 depends on the energy of the X-ray quanta. This is because on the one hand the spectrum emitted by the X-ray source already exhibits such a dependency and because on the other hand the object 4 attenuates the various energies to a different extent. In order to compensate for this effect, the spectrum which has been measured by the detector 6 and wherefrom the background radiation has been removed must be normalized to the transmitted spectrum. The transmitted spectrum can be derived from the output signal of the detector 5 which is arranged in front of the second diaphragm device 71 in the primary beam (denoted by a broken line). The electronic circuitry required for this purpose (the units 90 . . . 96) have been omitted from FIG. 1 for the sake of clarity. Normalization is performed in a circuit 95 in which the intensity measured by the detector 6 for each sub-range of the energy or the pulse transfer is divided by the transmitted intensity.

The energy or pulse transfer spectrum thus corrected can be displayed on a display unit 96. However, for cases where it is merely necessary to determine whether the object 4 (for example, a piece of luggage) contains a predetermined substance having a known pulse transfer spectrum, for example an explosive, it also suffices to compare the measured spectrum with the spectrum of the relevant substance which is stored in a further memory and to generate an alarm signal in the case of correspondence.

The function of the units 92, 94 and 95 can be realized by means of a microprocessor which can also control the entire execution of the measurement.

Figure 3:
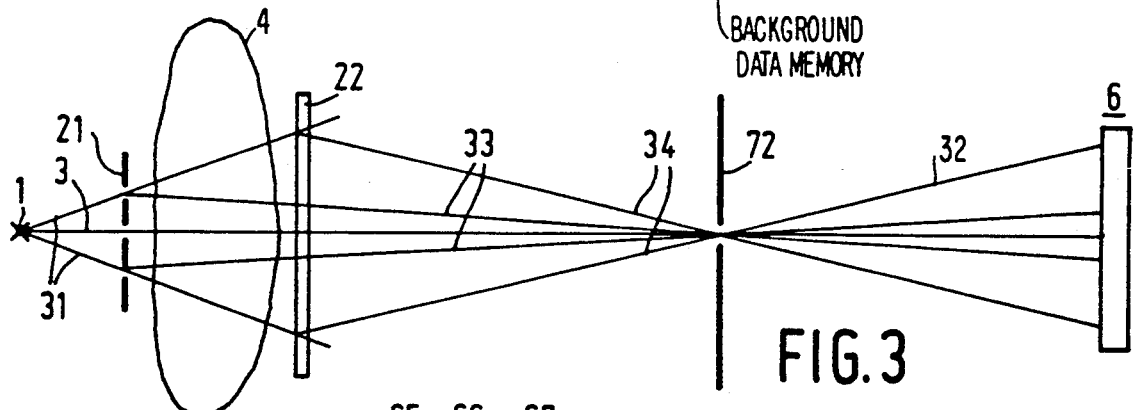
FIG. 3 shows a third embodiment.

In FIG. 3 there is arranged between the radiation source 1 and the examination zone again a first diaphragm device comprising a single diaphragm plate 21 having both a central point-shaped aperture for forming the small cross-section central beam and an annular ring-like aperture for forming the envelope of a primary annular radiation cone 31. After the examination zone 4 is a second diaphragm device comprising diaphragm plate 72 having a central aperture which is concentric with the annular aperture and which serves to form a secondary beam 32 which coincides with the symmetry axis of the cone. When the X-ray source operates with a voltage of 150 kV and the diaphragm plate 21 is situated at a distance of 200 mm from the radiation source, the annular aperture preferably has a diameter of 14 mm. This results in an angle of aperture of the radiation beam of 2°.

The examination zone is bounded here by an X-ray transparent plate or diaphragm 22 which is situated at a distance of, for example 250 mm from the plate 21. With this device, objects having a thickness of up to 250 mm can be examined. The diaphragm 72 is at a distance of for example, 850 mm from the diaphragm plate 22, which is substantially larger than the distance between this plate and the X-ray source 1. The radiation passing through this aperture is incident on a detector 6 which is situated at a distance of, for example 800 mm from the diaphragm 72.

Figure 4A:
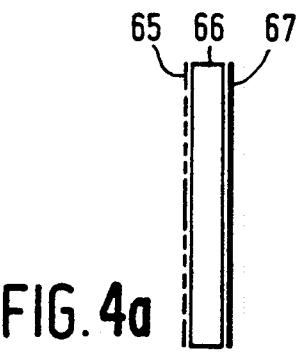
FIGS. 4a and 4b show a detector which is suitable for the device shown in FIG. 2.
Figure 4B:
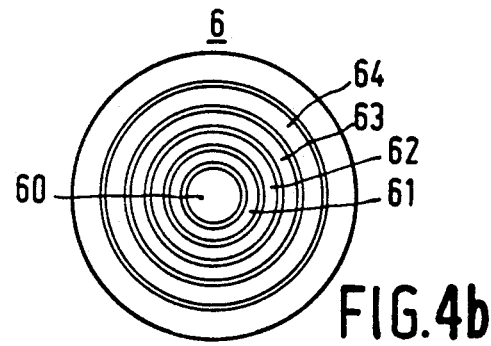

As appears from the FIGS. 4a and 4b this detector 6 comprises a circular detector crystal 66, one side of which is provided with a circular electrode 67 of corresponding dimensions, its other side being provided with a plurality of mutually concentric annular ring-like electrodes with a circular disc-like electrode in the centre. The electrodes are separated from one another by gaps of, for example 0.5 mm. The annular electrode 65 having the largest diameter carries ground potential, as does the electrode 67. Therefore, for the other electrodes this electrode acts as a guard electrode. The other ring-like electrodes constitute, together with the detector crystal 66 and the common electrode 67, a respective detector 60 . . . 64, the circular detector 60 in the centre being enclosed by four concentric, annular detectors 61, 62, 63 and 64.

The diameter of the central detector 60 is so small that it can be struck only by the primary beam passing through the diaphragm 72, but not by scattered radiation generated by the primary radiation cone 31 inside the examination zone defined by the plates 21, 22. The ring electrode 61 forming detector surrounding the detector 60 has a diameter such that it can be struck by scattered radiation which passes through the aperture of diaphragm 72 and which is generated by the primary radiation cone 31 in the first quarter of the examination zone which adjoins the diaphragm plate 21. Similarly, the second, the third and the fourth detectors (62, 63, 64, respectively) detect the scattered radiation generated by the primary radiation cone in the second quarter, the third quarter and the fourth quarter, respectively, of the examination zone.

In the device shown in FIG. 2 each of the detectors 61 . . . 64 of detector 6 are succeeded by the electronic evaluation circuitry 90 . . . 96. The central detector 60 of detector has the same function as the detector 5 in the device of FIG. 1 and FIG. 2.

The boundary rays 33 and 34 of the X-ray beam detected by the detector 6, are associated with the front and the rear edge, respectively, of the examination zone, in FIG. 3. It appears that the scattered radiation associated with the last quarter of the examination zone reaches the outer detector 64 at an angle which is larger than that at which the scattered radiation from the first quarter of the examination zone reaches the inner the detector 61. The differences, however, are substantially smaller than appears from FIG. 3 which is not to scale; for the dimensions given, the scattering angle is between 2.4° and 3.1°, so that substantially the same range of the pulse transfer can be determined by means of each of the detectors 61 . . . 64. This small scattering angle difference is due to the fact that the distance between the diaphragm 72 and the diaphragm 21 is substantially larger than their distance from the X-ray source 1. This comparatively large distance also ensures that each detector ring only receives scattered radiation which is associated with a very small scattering angle range. For example, the outer most 64 receives scattered radiation which deviates only approximately 0.1° from a mean scattering angle amounting to approximately 2.95°. The deviation is even smaller for the inner detectors.

The intensity of the scattered radiation measured by the detector 6 is higher and hence the measuring time is shorter as the aperture in the diaphragm 72 becomes larger. A large aperture in this disphragm, however, implies that each individual detector 61, 64 can be exposed to scattered radiation in a larger scattering angle range; this affects the accuracy of determination of the pulse transfer from the detector output signal. Therefore, the diameter of the aperture in diaphragm 72 is formed by a compromise between the measuring time and the accuracy of determination of the pulse transfer. A value which is suitable for the previously mentioned dimensions is approximately 3 mm.

Figure 5A:
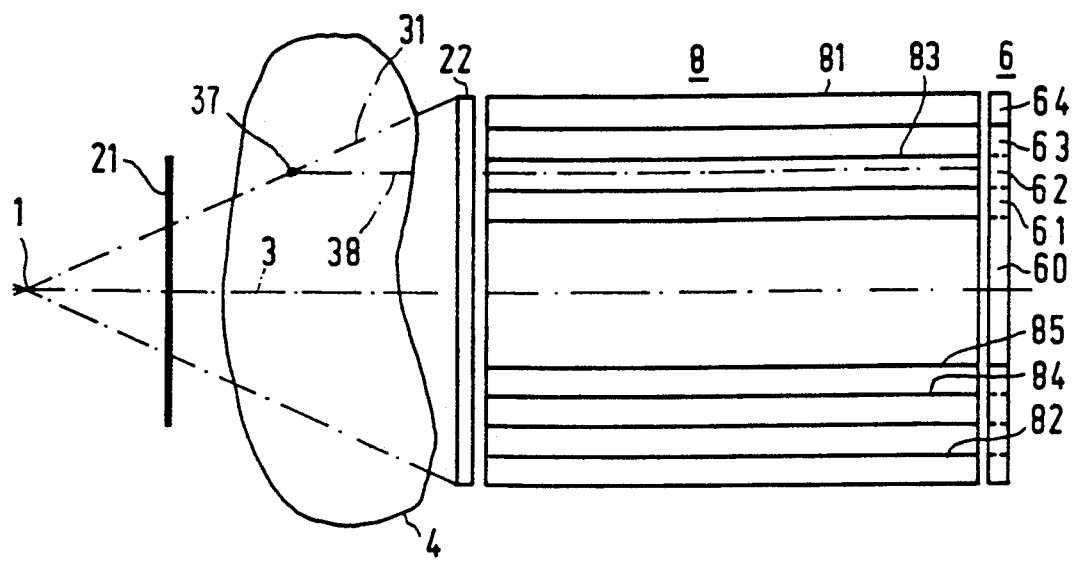
FIG. 5a shows a cross-section of a third preferred embodiment which contains the symmetry axis of the primary radiation cone.
Figure 5B:
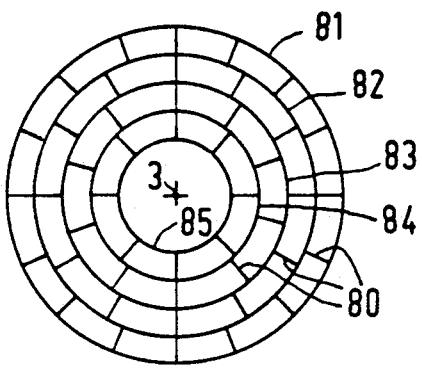
FIG. 5b is a cross-sectional view, taken at right angles thereto, through the same device.
Figure 6:
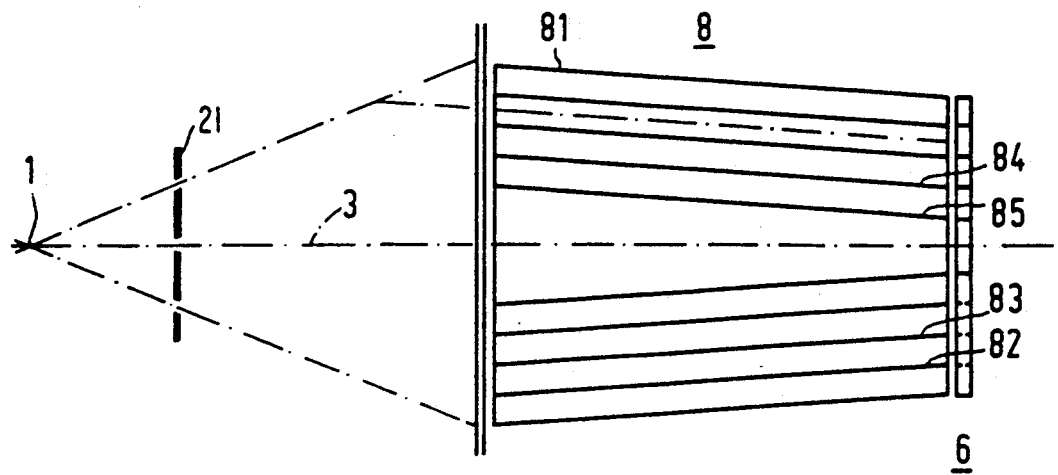
FIG. 6 shows an alternative version.

In the preferred embodiment of the invention which is shown in FIGS. 5a and 5b, and FIG. 6 the compromise between the measuring time and the accuracy of determination of the pulse transfer is substantially more attractive than in the device shown in FIG. 2. FIGS. 5a and 6 are not to scale; in reality the dimensions in the horizontal direction are substantially larger than those in the vertical direction.

The X-rays emitted by the polychromatic X-ray source 1 are incident on the diaphragm plate 21 which comprises a central aperture for the primary central beam along symmetry axis 3 and a concentric annular aperture which transmits the primary radiation cone 31 whose symmetry axis coincides with the central ray 3. The angle of the primary radiation cone 31, i.e. the angle between a ray of this cone originating from source 1 and the central ray 3 is comparatively small, for example 3°. The examination zone in which the object 4 is situated is defined by the diaphragm plate 21 and an X-ray transparent plate 22 which extends parallel thereto. The distance between the diaphragm 21 and the plate 22 may amount to 400 mm, the distance between the plate 22 and the X-ray source amounting to 600 mm.

The plate 22 is directly adjoined by a cylindrical collimator 8 which has a length of, for example 800 mm and which is arranged so as to be concentric with the symmetry axis 3. This collimator is formed by a number of mutually enclosing cylindrical collimator members 81...85 which have a circular cross-section. The drawing shows only five of such members, but more members may be present, for example 8. The resolution to be achieved in depth increases as the number of collimator members is greater.

The inner diameter of the outer collimator member 81 corresponds to the diameter of the circle described on the plate 22 by the primary radiation cone 31. The outer diameter of the inner collimator member 85 corresponds to the diameter of the annular aperture in the diaphragm 21. The collimator members, for example made of sheet steel, are as thin as possible but their thickness is sufficient to absorb the scattered radiation generated in the primary radiation beam 31. The same difference in diameter exists between neighbouring members.

The end opening of the collimator 8 which is remote from the plate 22 there is arranged the detector 6 which consists of a number of annular detectors 61...64, each of which measures exactly the scattered radiation passing between two neighbouring collimator members. The central detector 60 measures the intensity of the X-rays in the central beam 3. The signals are processed in the same way as described in detail with reference to FIG. 1.

The reference numeral 38 in FIG. 5a denotes a scattered beam which emerges from a scattering point 37 on the primary radiation cone 31 and which is situated within the object 4 to be examined. This scattered beam extends parallel to the central beam 3 or the symmetry axis and, therefore, corresponds to a scatter angle of 3°. It passes between the collimator members 83 and 84 and is incident on the detector ring 62. The scattered radiation from points which are situated nearer to the plate 22 passes through collimator members which are situated nearer to the periphery, the scattered radiation from points in the vicinity of the diaphragm 21 passing through the collimator members which are situated further inwards.

The drawing shows that a scattered beam which emerges from the same point as the beam 38 and which is also situated in the plane of drawing can deviate only slightly from the direction of the scattered beam 38, for example by 0.15°, because it is absorbed either by the collimator member 84 or by the collimator member 83 when the deviation is larger. However, when the scattered beam 38 is deflected in the tangential direction about the scatter point 37, i.e. out of the plane of drawing, substantially larger angular deviations may occur, without the scattered beam being absorbed by one of the collimator members 83, 84. The resultant variation of the scattering angle, however, is still comparatively small: when the scattered beam 38 is deflected through 9.5° about the scattering point 37 in the tangential direction, the resultant scattering angle variation is less than 0.05°. Therefore, with each scattering point there is associated a comparatively large arc of one of the annular detectors 61...64 so that for the same object 4, the same intensity of the X-ray source 1 and the same scattering angle inaccuracy the detector receives substantially more scattered radiation than in the device comprising a diaphragm as shown in FIG. 3.

Even though the effect of tangential angular deviations on the scattering angle is substantially smaller than the effect of radial angular deviations, it may be efficient to restrict also the maximum possible tangential angular deviations. To this end, baffles 80 are radially arranged between the collimator members 81...85, i.e. as indicated in FIG. 4b. These baffles are arranged in planes which intersect the symmetry axis 3. The distance between two neighbouring baffles, however, may be a multiple of the distance between two neighbouring collimator members. The distance between neighbouring baffles, each time arranged between the same collimator members, are substantially independent of whether the baffles are situated between the inner collimator members or between the outer collimator members. Consequently, as appears from the drawing more baffles are provided between the outer collimator members than between the inner collimator members.

The annular detectors 60...64 which may be circular may be semiconductor material comprising high-purity germanium and must correspond to the dimensions of the primary radiation cone in the examination zone. Therefore, the annular outer detector 64 should have a diameter of approximately 60 mm. Such semiconductor detectors are expensive. An embodiment shown in FIG. 6 allows for the use of detector rings of smaller diameter. It deviates from the embodiment shown in FIG. 5a merely in that conical collimator members are used instead of the cylindrical collimator members, the conical collimator members being tapered in the direction from the examination zone towards the detector, the collimator members are shaped so that the straight intersecting lines of the collimator members extend in parallel in a longitudinal cross-section containing the central beam 3. When the angle of aperture of the cones, on the envelope of which the collimator members 81...85 are situated amounts to, for example 1°, the diameter of the detector rings may be approximately 28 mm smaller than in the embodiments shown in FIG. 4a for dimensions which are otherwise the same.

In the embodiments shown in FIGS. 5a, 5b and 6 each detector (for example, 62) is associated with the space between neighbouring collimator members e.g. members (83, 84). However, the annular detectors can also be constructed so as to be wider, so that they detect the scattered radiation between a collimator member, for example, 83 and its next neighbour, but one 85. The resolution in depth is then reduced, but the signal-to-noise ratio is improved.

I claim:

1. A device for measuring the pulse transfer spectrum of X-ray quanta which are elastically scattered in an examination zone of an X-ray system comprising a polychromatic x-ray source on one side of the examination zone, said measuring device comprising:

a detector on the other side of the zone for measuring the energy of the X-ray quanta; and two apertured diaphragms which have a common symmetry axis and which transmit scattered radiation to the detector only within a given scattering angle range, a first diaphragm being between the examination zone and the X-ray source and a second diaphragm between the examination zone and the detector, the first diaphragm being constructed so that the X-rays transmitted therethrough form a conical envelope of a primary radiation cone, the second diaphragm being constructed so that scattered radiation produced in the examination zone is incident on the detector in an annular symmetrical fashion with respect to said axis of symmetry.

2. A device as claimed in claim 1, wherein the second diaphragm is constructed so that it defines a scattered radiation cone which is tapered in the direction from the examination zone towards the detector device.

3. A device as claimed in claim 1, wherein the second diaphragm is arranged at a distance from the examination zone as well as at a distance from the detector and whose aperture coincides with the symmetry axis.

4. A device as claimed in claim 1, wherein the second diaphragm comprises a plurality of mutually enclosing cylindrical collimator members which are concentric with the symmetry axis of the primary radiation cone.

5. A device as claimed in claim 4, wherein the detector comprises a plurality of concentric annular detectors.

6. A device as claimed in claim 5, wherein the diameters of the collimator members and the detectors are adapted to one another so that the scattered radiation passing between two collimator members is detected by one detector.

7. A device as claimed in claim 1, wherein the first diaphragm comprises an aperture on the symmetry axis, on the symmetry axis on the other side of the examination zone there being provided a further detector for measuring the transmitted radiation.

8. A device as claimed in claim 7, wherein the further detector measures the scattered radiation in an energy-resolution fashion.

9. A device as claimed in claim 7, wherein the further detector comprises a detector crystal in conjunction with the annular detectors.

10. A device as claimed in claim 3, wherein the distance between the detector and the examination zone is substantially larger than the distance between the X-ray source and the examination zone.

11. A device as claimed in claim 4, wherein between neighbouring collimator members baffles are arranged in planes which intersect at the symmetry axis.

12. A device as claimed in claim 3, wherein the detector comprises a plurality of concentric annular detectors.

13. A device as claimed in claim 2, wherein the first diaphragm comprises an aperture on the symmetry axis, on the symmetry axis on the other side of the examination zone there being provided a further detector for measuring the transmitted radiation.

14. A device as claimed in claim 4, wherein the distance between the detector and the examination zone is substantially larger than the distance between the X-ray source and the examination zone.

15. The device of claim 1 wherein each said diaphragms comprises at least one annular ring-like aperture concentric with said axis.

16. The device of claim 15 wherein the diaphragms have a further central aperture for passing a relatively narrow beam of said radiation within said cone.

17. The device of claim 1 wherein the first diaphragm has a ring-like annular aperture.

* * * * *